United States Patent
Uehara et al.

(10) Patent No.: US 6,334,935 B1
(45) Date of Patent: *Jan. 1, 2002

(54) DISTILLATION OF (METH) ACRYLOXY-BEARING ALKOXYSILANE

(75) Inventors: Katsuhiro Uehara; Mikio Endo; Tohru Kubota; Satoshi Uchida; Kanji Murofushi, all of Nakakubiki-gun (JP)

(73) Assignee: Shin-Etsu Chemical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/335,772

(22) Filed: Jun. 18, 1999

(30) Foreign Application Priority Data

Jun. 19, 1998 (JP) .............................. 10-189959

(51) Int. Cl.⁷ .............................. B01D 3/10; B01D 3/34; C07F 7/18; C07F 7/20
(52) U.S. Cl. .............................. 203/8; 203/21; 203/40; 203/72; 203/73; 203/89; 203/91; 203/98; 556/479
(58) Field of Search .............................. 203/89, 40, 91, 203/3, 98, 8, 21, 72, 73; 202/197, 205, 236; 159/901, DIG. 20, DIG. 16, 49, 6.1; 556/479, 440; 528/12, 21, 23

(56) References Cited

U.S. PATENT DOCUMENTS

| | | | | | |
|---|---|---|---|---|---|
| 4,304,920 A | * | 12/1981 | Arai et al. | .................. | 556/440 |
| 4,709,067 A | * | 11/1987 | Chu et al. | .................. | 556/440 |
| 5,049,636 A | * | 9/1991 | Wolfgruber et al. | .......... | 528/33 |
| 5,374,761 A | * | 12/1994 | Bank | .......................... | 556/471 |
| 5,391,673 A | * | 2/1995 | Ekeland et al. | ............... | 528/12 |
| 5,674,938 A | * | 10/1997 | Rautschek et al. | .......... | 528/847 |
| 5,977,226 A | * | 11/1999 | Dent et al. | .................. | 524/267 |

FOREIGN PATENT DOCUMENTS

| | | | |
|---|---|---|---|
| JP | 073 16164 | * | 12/1995 |
| JP | 09 095 491 | * | 4/1997 |
| JP | 1 10 35584 | * | 2/1999 |

OTHER PUBLICATIONS

Chemical Abstract, vol. 124, No. 19, May 6, 1996, Columbus, Ohio, US; Abstract No. 261350; Kawase, Y. et al., "Stabilization of Acrylic Organosilicon Compounds at Distillation".

European Search Report for EP 99 30 4539 with Annex to the European Search Report on EP Application No. EP 99 30 4539; JP 07–316164 A, published Dec. 5, 1995, JP 2980514B, published Nov. 12, 1999.

* cited by examiner

*Primary Examiner*—Virginia Manoharan
(74) *Attorney, Agent, or Firm*—Millen, White, Zelano & Branigan, P.C.

(57) ABSTRACT

A (meth)acryloxy-bearing alkoxysilane is isolated and purified to a high purity by distilling a reaction solution containing the (meth)acryloxy-bearing alkoxysilane in a thin-layer distillation device at a temperature of 90–160° C. and a vacuum of 1–15 mmHg. The resulting alkoxysilane product does not give rise to the quality problem that the product will gradually whiten during storage owing to contact with air. The occurrence of self-polymerization of the alkoxysilane is restrained.

21 Claims, No Drawings

DISTILLATION OF (METH) ACRYLOXY-BEARING ALKOXYSILANE

This invention relates to a commercially advantageous method for distilling an acryloxy or methacryloxy-bearing alkoxysilane.

BACKGROUND OF THE INVENTION

Acryloxy or methacryloxy-bearing alkoxysilanes are widely used in the industry as silane coupling agents, novel polymerizable monomers and the like since they possess a polymerizable functional group in the form of an acryloxy or methacryloxy group in the structure.

Commonly employed for the industrial mass-scale purification of the acryloxy or methacryloxy-bearing alkoxysilane is a method of isolating and purifying the alkoxysilane under high temperature/long time distillation conditions, known as long thermal history distillation conditions, using a distillation device having a reboiler combined with a multi-stage distillation column.

The product obtained by this purifying method, however, suffers from the quality problem that the product in a container for storage gradually becomes white turbid if the product has a chance of contact with air as can occur during manipulations such as opening and closing of a cap of the container and transfer from the container. This phenomenon is herein referred to as an open-air whitening phenomenon because the product experiences prominent whitening when it is open to air. The (meth)acryloxy-bearing alkoxysilane products, though they have been purified, often receive unexpected claims on their quality because of their visual changes caused by the open-air whitening phenomenon.

The open-air whitening phenomenon can be prevented by secondary countermeasures such as by treating with adsorbents such as active carbon and silica gel or fully purging with nitrogen at the end of manipulation for air-blocked storage. These countermeasures are not only unsatisfactory solutions, but also impose more burdens because the treatment or operation following purification becomes very complicated. No essential solutions have been available to the open-air whitening phenomenon. Therefore, it has long been desired to establish an effective solution to the open-air whitening phenomenon.

Further, since (meth)acryloxy-bearing alkoxysilanes are thermally unstable compounds having self-polymerization capability, the above-described purifying method with a long thermal history has a probability that polymerization will occur during the purifying process, which can cause clogging of the distillation column or thickening or gelation of the liquid in the reboiler.

For the purpose of avoiding these problems, a variety of polymerization inhibitors have been developed. None of the polymerization inhibitors have a fully satisfactory function. When the polymerization inhibitors are blended in (meth) acryloxy-bearing alkoxysilane products, some cause quality problems undesirable in their applications like coloring and a decline of polymerization capability, and some are toxic or hazardous. For this and other reasons, the polymerization inhibitors do not achieve a satisfactory improvement. There is a desire to have a short thermal history method of purifying (meth)acryloxy-bearing alkoxysilanes while essentially suppressing the self-polymerization capability thereof.

SUMMARY OF THE INVENTION

An object of the invention is to provide a method for isolating, by distillation, a (meth)acryloxy-bearing alkoxysilane of high purity in a commercially advantageous manner while suppressing the occurrence of self-polymerization during the process and minimizing the potential open-air whitening phenomenon of the product upon exposure to air.

The inventor has found that by subjecting a reaction solution containing an acryloxy or methacryloxy-bearing alkoxysilane represented by the general formula (1):

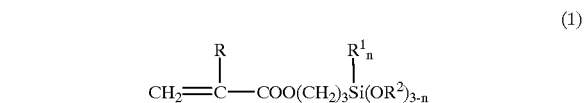

(1)

wherein R is hydrogen or methyl, $R^1$ and $R^2$ each are alkyl of 1 to 4 carbon atoms, and n is an integer of 0 to 2, to thin-layer distillation at a temperature up to 160° C. and a vacuum of up to 15 mmHg, the acryloxy or methacryloxy-bearing alkoxysilane can be purified to a high purity while suppressing the occurrence of self-polymerization during the process and minimizing the potential open-air whitening phenomenon upon exposure to air.

The development process of open-air whitening was investigated. Namely, minute quantities of impurities in a (meth)acryloxy-bearing alkoxysilane product were separated by gas chromatography and identified by mass spectroscopy, thereby examining the behavior of minute impurities before and after the open-air whitening phenomenon. As a result, it was found that a causative substance (A) represented by the following formula (2):

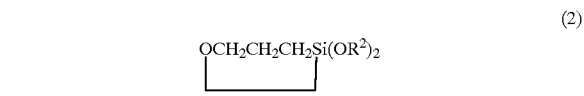

(2)

wherein $R^2$ is as defined above forms in a minor amount as a by-product during distillation under long thermal history conditions and is left admixed in the product isolated by distillation. Upon contact with air of the product containing causative substance (A), the causative substance undergoes selective hydrolytic condensation reaction with moisture in the air to form fine gel-like fractions, which brings about the open-air whitening phenomenon. As the thermal history during distillation becomes greater (higher temperature and/or longer time), the amount of causative substance (A) by-product increases, with which the degree of whitening increases.

Paying attention to the above-described causative substance (A), the inventor investigated how to suppress the formation of this substance. Surprisingly, it has been found that by effecting distillation under the controlled conditions in a thin-layer distillation device, causative substance (A) is not produced at all and there is obtained a product which will be free from open-air whitening. The controlled distillation is also effective for substantially avoiding self-polymerization. Therefore, the alkoxysilane can be purified to a high purity through a simple process without a need for cumbersome post-treatment. Additionally, continuous distillation becomes possible, with an improvement in hourly productivity.

The invention provides a method for isolating and purifying an acryloxy or methacryloxy-bearing alkoxysilane of formula (1), comprising the step of distilling a reaction solution containing the acryloxy or methacryloxy-bearing alkoxysilane in a thin-layer distillation device at a temperature of up to 160° C. and a vacuum of up to 15 mmHg.

DESCRIPTION OF THE PREFERRED EMBODIMENTS

The method for distilling an isolating an acryloxy or methacryloxy-bearing alkoxysilane according to the invention starts with a reaction solution containing the alkoxysilane. The (meth)acryloxy-bearing alkoxysilane is represented by formula (1):

(1)

R is hydrogen or a methyl group, each of $R^1$ and $R^2$ is an alkyl group of 1 to 4 carbon atoms, such as methyl, ethyl, propyl or butyl, and n is an integer of 0 to 2.

Illustrative examples of the (meth)acryloxy-bearing alkoxysilane of formula (1) include
3-acryloxypropyltrimethoxysilane,
3-acryloxypropyltrimethoxysilane,
3-methacryloxypropyltrimethoxysilane,
3-methacryloxypropyltriethoxysilane,
3-acryloxypropylmethyldimethoxysilane,
3-acryloxypropylmethyldiethoxysilane,
3-methacryloxypropylmethyldimethoxysilane, and
3-methacryloxypropylmethyldiethoxysilane.

With respect to the reaction solution containing the (meth)acryloxy-bearing alkoxysilane of formula (1), its synthesis process is not critical. There may be used any of reaction solutions which are synthesized by various conventional processes and optionally concentrated. Preferred is a reaction solution in which the concentration of the (meth)acryloxy-bearing alkoxysilane of formula (1) is at least 70% by weight and the concentration of impurities having a lower boiling point than the alkoxysilane is not more than about 1% by weight. The reaction solution may be once distilled before it is subjected to distillation according to the invention.

The thin-layer distillation device used herein may be a device of commonly known specification having an agitation drive section of spreading the reaction solution in thin layer form and a heating and evaporation/condensation section of heating the reaction solution thin layer under vacuum for evaporation and condensation. For any of such devices, distillation operation may be carried out by a procedure commonly taken for the operation of that device. The thin-layer distillation device may be a well-known one, preferably an evaporator of the centrifugal type in which the feed solution is centrifugally spread by an internal agitating blade over a heating section to form a thin layer, which may be of the lateral or upright type. The heating section may be either a cylindrical type or a tapered type while its heat transfer area is not critical. Among others, an upright falling-film evaporator comprising a cylindrical heating section and a wiper-like agitating blade wherein the tip of the agitating blade Is centrifugally urged against the surface of the heating section for scraping the surface is preferable because evaporation to a high concentration is possible.

The method of the invention Is characterized by effecting thin-layer distillation in the above-described thin-layer distillation device under a vacuum of up to 15 mmHg, preferably 1 to 15 mmHg while keeping the heating section at a temperature of up to 160° C., preferably 90 to 160° C. The objects of the invention cannot be achieved at a vacuum of higher than 15 mmHg or a heating section temperature of higher than 160° C., because the amount of causative substance (A) by-product gradually increases so that the resulting product will become subject to open-air whitening and the percent occurrence of polymerization is promoted by the heat. The distillation time may be adjusted as appropriate in accordance with the feed amount. Depending on the specifications of a particular thin-layer distillation device used, the amount of the solution fed is preferably set between the lower limit at which the thin-layer formed thereby becomes discontinuous and the upper limit at which the rate of evaporation reaches saturation and increases no more.

According to the invention, the feed solution is distilled in the thin-layer distillation device under the above-specified conditions while the remaining conditions may be adjusted as appropriate.

First, a mist separator may be connected to the thin-layer distillation device for separating off mist from the feed solution, if necessary. Specifically, a column of any desired height packed with a commercially available distillation-promoting packing is connected in a vapor line from the thin-layer distillation device to a condenser. Alternatively, the mist separator is mounted upstream of an upper vapor outlet within an upright evaporator.

Where the feed solution to be distilled contains components having a lower boiling point than the main component, impurities and solvents, a concentration step is preferably carried out, prior to the isolation and purification of the main component, to thereby reduce the concentration of such undesirable components to less than about 1% by weight. This concentration step may be carried out using the thin-layer distillation device used for distillation. The concentrating conditions are not critical although an internal temperature of up to 160° C. and a vacuum of up to 50 mmHg are desirable. Since a too low vacuum would cause the trouble of a vacuum pump and the purge out of the system beyond the collecting capacity of the condenser and increase the amount of the end component distilled out, bringing about substantial losses, a vacuum in the range of 10 to 50 mmHg is preferable. By carrying out the concentration step in the thin-layer distillation device, a large volume of the reaction solution can be concentrated within a short time and the undesirable polymerization during the concentration step can be alleviated.

Prior to the admission of the reaction solution into the thin-layer distillation device, it may be preheated if desired. The preheating temperature of the reaction solution is not critical as long as it is below 120° C.

If evaporation to a high concentration cannot be accomplished by one pass in the distillation step according to the invention, the concentrated residue discharge is preferably fed back to the thin-layer distillation device for distillation again. This recycle distillation achieves a high percent recovery.

The flow rate of the feed solution is arbitrarily selected in accordance with the scale and specifications of a particular thin-layer distillation device used and not: generally limited. The optimum range of feed rate within which a maximum evaporation rate is achieved depends on a particular device, and too high or too low flow rates are undesirable. It is thus recommended to previously determine an optimum combination of a feed rate with an evaporation rate for a particular device.

Further, for restraining the (meth)acryloxy-bearing alkoxysilane from self-polymerization during distillation, a conventional well-known polymerization inhibitor may be added to the reaction solution in such an amount as not to raise a new quality problem to the alkoxysilane isolated and purified by the method of the invention.

Examples of the polymerization inhibitor include phenolic compounds such as hydroquinone and hydroquinone monomethyl ether; hindered phenols such as 4-methyl-2,6-d-t-butylphenol, 2,2'-methylenebis(4-methyl-6-t- butylphenol.), 2,2'-methylenebis(4-ethyl-6-t-butylphenol), 4,4'-butylidenebis(6-t-butyl-m-cresol), 1,3,5-trimethyl-2,4,6-tris(3,5-di-t-butyl-4-hydroxybenzyl)benzene, tris(3,5-di-t-butyl-4-hydroxybenzyl)isocyanurate, 2,2-thio-diethylene-bis[3-(3,5-di-t-butyl-4-hydroxyphenyl) propionatel], and 2,2'-methylenebis(4-methyl-6-t-butylphenol)monoacrylate; copper compounds such as cuprous chloride, cupric chloride, cuprous oxide, cupric oxide, copper sulfate, and copper dimethyldithiocarbamate; sulfur-containing compounds such as phenothiazine, nitrogen-containing compounds such as octylated diphenylamine; and phosphorus-containing compounds. These polymerization inhibitors may be used alone or in admixture of two or more. The amount of the polymerization inhibitor added is not critical although it is preferably added in an amount of 0.01 to 10% by weight, more preferably 0.1 to 1% by weight, based on the weight of the compound of formula (1) in the reaction solution.

In general, the polymerization inhibitor is added to and dissolved in the reaction solution before the solution is fed to the thin-layer distillation device. As long as the admixing of the polymerization inhibitor into the product does not give rise to a quality problem, the polymerization inhibitor as a solution in the product or a suitable solvent may be introduced midway the vapor line or to the stream after condensation in the condenser.

An inert gas containing molecular oxygen, for example, air diluted with nitrogen may be introduced into the system, if necessary, for the purpose of inhibiting polymerization. The amount of the oxygen-containing inert gas is not particularly limited insofar as it is below the lower limit of the explosive range. It is effective to introduce the inert gas to the vapor line although the introducing portion is not limited thereto.

In one preferred embodiment of the invention, to the reaction solution containing the (meth)acryloxy-bearing alkoxysilane to be fed to the thin-layer distillation device, a liquid having a higher boiling point than the alkoxysilane is added insofar as the objects of the invention are not impaired. The addition of the high-boiling liquid alleviates the problem that the residues (Including the polymerization inhibitor, catalyst and high-boiling impurities) left after intense concentration precipitate and deposit on the heating section inner wall of the distillation device and the discharge line, enabling long-term operation. Such high boiling liquids are, for example, turbine oil, liquid paraffin, and silicone oil.

There has been described a method for isolating and purifying a (meth)acryloxy-bearing alkoxysilane by thin-layer distillation under specific conditions. The resulting alkoxysilane product does not give rise to the quality problem that the product will gradually whiten during storage owing to contact with air (essentially moisture in air). Since the occurrence of self-polymerization of the alkoxysilane is restrained, the method is effective for preventing line blockage and yield drops by gel formation and improving the productivity. Therefore, the (meth)acryloxy-bearing alkoxysilane of high purity is obtained in a commercially advantageous manner.

EXAMPLE

Examples of the invention are given below by way of illustration and not by way of limitation.

Example 1

The thin-layer distillation device used was an upright scraping blade type rotary thin-layer evaporator commercially available from Shibata Scientific Equipment Industry K.K.

To 900 g of a reaction solution of 97.8% by weight 3-methacryloxypropyltrimethoxysilane which had been conventionally synthesized and concentrated, were added 0.9 g of 4-methyl-2,6-di-tert-butylphenol and 0.45 g of copper dimethyldithiocarbamate as polymerization inhibitors. The solution was subjected to continuous thin-layer distillation by feeding the solution to the evaporator over 3.2 hours while operating the evaporator at a vacuum of 5 to 10 mmHg and a heating zone temperature of 150° C. in a conventional manner. As a result, 792 g of 3-methacryloxypropyltrimethoxysilane was distilled and purified while 105 g of non-volatile matter was collected as the residue.

On gas chromatography analysis, the purified 3-methacryloxypropyltrimethoxysilane product had a purity of 99.1% and the content of causative substance (A) of formula (1) was nil. When exposed to air overnight, this purified product remained clear without giving rise to open-air whitening. Within the evaporator, the formation of a polymer was not observed.

Comparative Examples 1–4

The distillation device used was a 1-liter glass flask serving as a distillation kettle which was equipped with a distillation column having an outer diameter of 20 mm and a height of 500 mm and packed with SUS-304 McMahon packing, which was, in turn, connected at the top to a fractionating column and a condenser.

To 900 g of a reaction solution of 97.8% by weight 3-methacryloxypropyltrimethoxysilane which had been conventionally synthesized and concentrated, were added 0.9 g of 4-methyl-2,6-di-tert-butylphenol and 0.45 g of copper dimethyldithiocarbamate as polymerization inhibitors. The solution was admitted into the distillation device where batchwise precision distillation was carried out in a conventional manner while setting at the vacuum and kettle temperature shown below. The distillation time was about 10 hours in each run.

The products purified under the following set of distilling conditions were analyzed for composition and examined for outer appearance changes when exposed to air overnight.

Comparative Example 1:
  vacuum 6 mmHg, kettle temp. 130° C.
  main component 99.5%, causative substance (A) 0.0376%
  whitened upon air exposure Comparative Example 2:
  vacuum 9 mmHg, kettle temp. 140° C.
  main component 99.4%, causative substance (A) 0.0562%
  whitened upon air exposure Comparative Example 3:
  vacuum 14 mmHg, kettle temp. 150° C.
  main component 99.1%, causative substance (A) 0.0978%
  deeply whitened upon air exposure Comparative Example 4:
  vacuum 23 mmHg, kettle temp. 155° C.
  main component 98.9%, causative substance (A) 0.2154%
  more deeply whitened upon air exposure; Some whitened fractions agglomerated into gel which precipitated and settled down when allowed to stand.

For all the samples, when they were exposed to air and allowed to stand in air, the progress of whitening and the reduction of causative substance (A) were observed. The progress of whitening stopped when causative substance (A) disappeared. Next, the sample in which the progress of whitening stopped with the loss of causative substance (A) was filtered whereupon the clear supernatant no longer whitened when exposed to air again.

These results indicate that in the prior art conventional distillation procedure entailing a long thermal history, a minute amount of causative substance (A) forms as a by-product, which triggers open-air whitening. The more the amount of causative substance (A), the greater becomes the degree of whitening. If the amount of causative substance (A) is nil, no whitening occurs. It was also found that the amount of causative substance (A) increases as the distillation temperature rises.

Example 2

The thin-layer distillation device used was an upright scraping blade type rotary thin-layer evaporator as used in Example 1.

To 692.3 g of a reaction solution of 87% by weight 3-acryloxypropyltrimethoxysilane which had been conventionally synthesized and concentrated, was added 0.69 g of 4-methyl-2,6-di-tert-butylphenol as a polymerization inhibitor. The solution was subjected to continuous thin-layer distillation by feeding the solution to the evaporator over 4.1 hours while operating the evaporator at a vacuum of 5 mmHg and a heating zone temperature of 134° C. in a conventional manner. As a result, 448 g of 3-acryloxypropyltrimethoxysilane was distilled and purified while 244 g of non-volatile matter was collected as the residue.

On gas chromatography analysis, the purified 3-acryloxypropyltrimethoxysilane product had a purity of 98.6% and the content of causative substance (A) was trace. When exposed to air, this purified product remained clear without giving rise to open-air whitening. Within the evaporator, the formation of a polymer was not observed.

Comparative Example 5

The distillation device used was a 1-liter glass flask serving as a distillation kettle which was equipped with a distillation column having an outer diameter of 20 mm and a height of 500 mm and packed with SUS-304 McMahon packing, which was, in turn, connected at the top to a fractionating column and a condenser.

To 1000 g of a reaction solution of 82% by weight 3-acryloxypropyltrimethoxysilane which had been conventionally synthesized and concentrated, were added 1 g of 4-methyl-2,6-di-tert-butylphenol and 3 g of copper dimethyldithiocarbamate as polymerization inhibitors. The solution was admitted into the distillation device where batchwise precision distillation was carried out for about 10 hours in a conventional manner while setting at a vacuum of 5 to 10 mmHg and a kettle temperature of 130 to 145° C. As a result, 670 g of 3-acryloxypropyltrimethoxysilane was distilled and purified while 88 g of the fore-running and 221 g of non-volatile matter were collected as the residue.

On gas chromatography analysis, the purified 3-acryloxypropyltrimethoxysilane product had a purity of 97.9% and the content of causative substance (A) was 0.98%. When exposed to air, this purified product whitened within only 30 minutes. After overnight exposure, a large amount of white gel precipitated and settled as agglomerates on the bottom.

When the same procedure was repeated except that the copper dimethyldithiocarbamate polymerization inhibitor was omitted, the liquid in the kettle gelled during distillation.

Comparative Example 6

The thin-layer distillation device used was an upright scraping blade type rotary thin-layer evaporator as used in Example 1.

To 692.3 g of a reaction solution of 87% by weight 3-acryloxypropyltrimethoxysilane which had been conventionally synthesized and concentrated, was added 0.69 g of 4-methyl-2,6-di-tert-butylphenol as a polymerization inhibitor. The solution was subjected to continuous thin-layer distillation by feeding the solution to the evaporator over 4.5 hours while operating the evaporator at a vacuum of 20 mmHg and a heating zone temperature of 160 to 165° C in a conventional manner. As a result, 473 g of 3-acryloxypropyltrimethoxysilane was distilled and purified while 213 g of non-volatile matter was collected as the residue.

On gas chromatography analysis, the purified 3-acryloxypropyltrimethoxysilane product had a purity of 96.3% and the content of causative substance (A) was 0.16%. When exposed to air overnight, this purified product gave rise to open-air whitening.

Example 3

The thin-layer distillation device used was an lateral rotary thin-layer evaporator having a heat transfer area of 1 m².

To a reaction solution of 63.8% by weight 3-methacryloxypropyltrimethoxysilane which had been conventionally synthesized and concentrated, were added 500 ppm of 4-methyl-2,6-di-tert-butylphenol and 1000 ppm of copper dimethyldithiocarbamate as polymerization inhibitors. The solution was subjected to continuous thin-layer distillation (for concentration) by feeding the solution to the evaporator over 39 hours at a rate of 58 kg/hr while operating the evaporator at a vacuum of 20 mmHg and a heating zone temperature of 155° C. in a conventional manner. There was obtained about 1,400 kg of a concentrate containing 98.5% of 3-methacryloxypropyltrimethoxysilane.

This concentrate was subjected to continuous thin-layer distillation (for isolation and purification) by feeding the concentrate to the evaporator over 15 hours at a rate of 95 kg/hr while operating the evaporator at a vacuum of 12 mmHg and a heating zone temperature of 155° C. in a conventional manner. As a result, about 1,100 kg of 3-methacryloxypropyltrimethoxysilane was distilled and purified while about 300 kg of non-volatile matter was collected as the residue.

On gas chromatography analysis, the purified 3-methacryloxypropyltrimethoxysilane product had a purity of 99.3% and the content of causative substance (A) was nil. When exposed to air overnight, this purified product remained clear without giving rise to open-air whitening. Within the evaporator, the formation of a polymer was not observed.

Next, about 300 kg of the non-volatile matter resulting from the thin-layer distillation (for isolation and purification) was subjected again to continuous thin-layer distillation (for recovery and purification) by feeding the non-volatile matter to the evaporator over 3 to 4 hours at a rate of 95 kg/hr while operating the evaporator at a vacuum of 12 mmHg and a heating zone temperature of 155° C. in a conventional manner. As a result, about 220 kg of 3-methacryloxypropyltrimethoxysilane was distilled and purified while about 80 kg of non-volatile matter was collected as the residue.

On gas chromatography analysis, the purified 3-methacryloxypropyltrimethoxysilane product had a purity of 99.1% and the content of causative substance (A) was nil. When exposed to air overnight, this purified product remained clear without giving rise to open-air whitening. Within the evaporator, the formation of a polymer was not observed.

Example 4

The thin-layer distillation device used was an upright scraping blade type rotary thin-layer evaporator having a heat transfer area of 0.3 m².

To a concentrate of 95% by weight 3-methacryloxypropyltrimethoxysilane which had been conventionally synthesized and concentrated, were added 500 ppm of 4-methyl-2,6-di-tert-butylphenol and 1000 ppm of copper dimethyldithiocarbamate as polymerization inhibitors. The concentrate was subjected to continuous thin-layer distillation (for isolation and purification) by feeding the concentrate to the evaporator at a feed rate of 45 to 50 kg/hr over several hours while operating the evaporator at a vacuum of 5 mmHg and a heating zone temperature of 150° C. in a conventional manner. As a result, about 42 to 47 kg/hr of 3-methacryloxypropyltrimethoxysilane was distilled and purified while about 3 kg/hr of non-volatile matter was collected as the residue.

On gas chromatography analysis, the purified 3-methacryloxypropyltrimethoxysilane product had a purity of at least 99% and the content of causative substance (A) was nil. When exposed to air overnight, this purified product remained clear without giving rise to open-air whitening. Within the evaporator, the formation of a polymer was not observed.

Example 5

Using the same system and procedure as in Example 4 except that the vacuum during distillation was changed to 10 mmHg, continuous thin-layer distillation (for isolation and purification) was carried out over several hours. As a result, about 40 to 44 kg/hr of 3-methacryloxypropyltrimethoxysilane was distilled and purified while about 5 kg/hr of non-volatile matter was collected as the residue.

On gas chromatography analysis, the purified 3-methacryloxypropyltrimethoxysilane product had a purity of at least 99% and the content of causative substance (A) was nil. When exposed to air overnight, this purified product remained clear without giving rise to open-air whitening. Within the evaporator, the formation of a polymer was not observed. Example 6

Using the same system and procedure as in Example 4 except that the distillation conditions were changed to a vacuum of 10 mmHg and a heating zone temperature of 160° C., continuous thin-layer distillation (for isolation and purification) was carried out over several hours. As a result, about 42 to 47 kg/hr of 3-methacryloxypropyltrimethoxysilane was distilled and purified while about 3 kg/hr of non-volatile matter was collected as the residue.

On gas chromatography analysis, the purified 3-methacryloxypropyltrimethoxysilane product had a purity of at least 99% and the content of causative substance (A) was nil. When exposed to air overnight, this purified product remained clear without giving rise to open-air whitening. Within the evaporator, the formation of a polymer was not observed.

Japanese Patent Application No. 10-189959 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for distilling an acryloxy or methacryloxy-bearing alkoxysilane represented by formula (1):

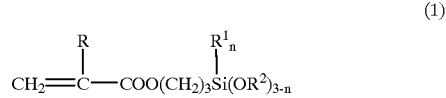

wherein R is hydrogen or methyl, $R^1$ and $R^2$ each are alkyl of 1 to 4 carbon atoms, and n is an integer of 0 to 2, said method comprising:

distilling a reaction solution containing said acryloxy or methacryloxy-bearing alkoxysilane in a thin-layer distillation device at a temperature of 90°–160° C. and a vacuum of 1 to 15 mmHg, wherein a mist separator is connected to said thin-layer distillation device for separating off mist from the reaction solution.

2. The method of claim 1, wherein in formula (1), both $R^1$ and $R^2$ are methyl and n is 0.

3. A method according to claim 1, wherein said acryloxy or methacryloxy-bearing alkoxysilane is:
   3-acryloxypropyltrimethoxysilane,
   3-acryloxypropyltrimethoxysilane,
   3-methacryloxypropyltrimethoxysilane,
   3-methacryloxypropyltriethoxysilane,
   3-acryloxypropylmethyldimethoxysilane,
   3-acryloxypropylmethyldiethoxysilane,
   3-methacryloxypropylmethyldimethoxysilane, or
   3-methacryloxypropylmethyldiethoxysilane.

4. A method according to claim 1, wherein the concentration of said acryloxy or methacryloxy-bearing alkoxysilane of formula (1) in said reaction solution is at least 70% by weight, and said reaction solution optionally contains impurities having a boiling point lower than that of said alkoxysilane and the concentration of said impurities in said reaction solution is not more than 1% by weight.

5. A method according to claim 1, wherein said thin-layer distillation device is a centrifugal evaporator in which the reaction solution is centrifugally spread by an internal agitating blade over a heating section to form a thin layer.

6. A method according to claim 5, wherein said thin-layer distillation device is an upright centrifugal evaporator.

7. A method according to claim 5, wherein said thin-layer distillation device is a lateral centrifugal evaporator.

8. A method according to claim 1, wherein said thin-layer distillation device is an upright falling-film evaporator comprising a cylindrical heating section and a wiper-like agitating blade wherein the tip of said agitating blade is centrifugally urged against the surface of said heating section for scraping the surface thereof.

9. A method according to claim 1, wherein said thin-layer distillation device is an upright evaporator and said mist separator is mounted upstream of an upper vapor outlet within said upright evaporator.

10. A method according to claim 1, wherein said mist separator is a column containing distillation-promoting packing, said column being connected to a vapor line between said thin-layer distillation device and a condenser.

11. A method according to claim 1, wherein, prior to distilling of said reaction solution into said thin-layer distillation device, said reaction solution is preheated.

12. A method according to claim 1, wherein concentrated residue discharged from said thin-layer distillation device is recycled back to said thin-layer distillation device.

13. A method according to claim 1, wherein a polymerization inhibitor is added to said reaction solution to inhibit self-polymerization of the acryloxy or methacryloxy-bearing alkoxysilane.

14. A method according to claim 13, wherein said polymerization inhibitor is added in an amount of 0.01–10% by weight, based on the weight of the acryloxy or methacryloxy-bearing alkoxysilane of formula (1) in said reaction solution.

15. A method according to claim 14, wherein said polymerization inhibitor is hydroquinone, hydroquinone monomethyl ether, 4-methyl-2,6-di-t-butylphenol, 2,2'-methylenebis(4-methyl-6-t-butylphenol), 2,2'-methylenebis(4-ethyl-6-t-butylphenol), 4,4'-butylidenebis(6-t-butyl-m-cresol), 1,3,5-trimethyl-2,4,6-tris(3,5-di-t-butyl-4-hydroxybenzyl)benzene, tris(3,5-di-t-butyl-4-hydroxybenzyl)isocyanurate, 2,2-thio-diethylene-bis[3-(3,5-di-t-butyl4-hydroxyphenyl) propionate], 2,2-methylenebis(4-methyl-6-t-butylphenol)monoacrylate, cuprous chloride, cupric chloride, cuprous oxide, cupric oxide, copper sulfate, copper dimethyldithiocarbamate, phenothiazine, octylated diphenylamine, or mixtures thereof.

16. A method according to claim 13, wherein said polymerization inhibitor is hydroquinone, hydroquinone monomethyl ether, 4-methyl-2,6-di-t-butylphenol, 2,2'-methylenebis(4-methyl-6-t-butylphenol), 2,2'-methylenebis(4-ethyl-6-t-butylphenol), 4,4'-butylidenebis(6-t-butyl-m-cresol), 1,3,5-trimethyl-2,4,6-tris(3,5-di-t-butyl-4-hydroxybenzyl)benzene, tris(3,5-di-t-butyl-4-hydroxybenzyl)isocyanurate, 2,2-thio-diethylene-bis[3-(3,5-di-t-butyl-4-hydroxyphenyl)propionate], 2,2-methylenebis(4-methyl-6-t-butylphenol)monoacrylate, cuprous chloride, cupric chloride, cuprous oxide, cupric oxide, copper sulfate, copper dimethyldithiocarbamate, phenothiazine, octylated diphenylamine, or mixtures thereof.

17. A method according to claim 13, wherein said polymerization inhibitor is a phenolic compound, a hindered phenol, a copper compound, a sulfur-containing compound, a nitrogen-containing compound, a phosphorous-containing compound, or mixtures thereof.

18. A method for distilling an acryloxy or methacryloxy-bearing alkoxysilane represented by formula (1):

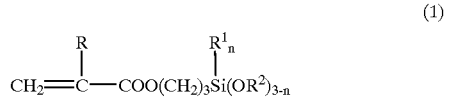

(1)

wherein R is hydrogen or methyl, $R^1$ and $R^2$ each are alkyl of 1 to 4 carbon atoms, and n is an integer of 0 to 2, said method comprising:
   distilling a reaction solution containing said acryloxy or methacryloxy-bearing alkoxysilane in a thin-layer distillation device at a temperature of 90°–160° C. and a vacuum of 1 to 15 mmHg, wherein said acryloxy or methacryloxy-bearing alkoxysilane is:
   3-acryloxypropyltrimethoxysilane,
   3-acryloxypropyltriethoxysilane,
   3-methacryloxypropyltrimethoxysilane,
   3-methacryloxypropyltriethoxysilane,
   3-acryloxypropylmethyldimethoxysilane,
   3-acryloxypropylmethyldiethoxysilane,
   3-methacryloxypropylmethyldimethoxysilane, or
   3-methacryloxypropylmethyldiethoxysilane.

19. A method for distilling an acryloxy or methacryloxy-bearing alkoxysilane represented by formula (1):

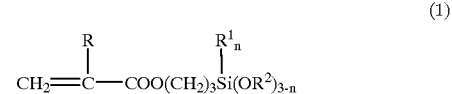

(1)

wherein R is hydrogen or methyl, $R^1$ and $R^2$ each are alkyl of 1 to 4 carbon atoms, and n is an integer of 0 to 2, said method comprising:
   distilling a reaction solution containing said acryloxy or methacryloxy-bearing alkoxysilane in a thin-layer distillation device at a temperature of 90°–160° C. and a vacuum of 1 to 15 mnHg,
   wherein said thin-layer distillation device is a centrifugal evaporator in which the reaction solution is centrifugally spread by an internal agitating blade over a heating section to form a thin layer.

20. A method for distilling an acryloxy or methacryloxy-bearing alkoxysilane represented by formula (1):

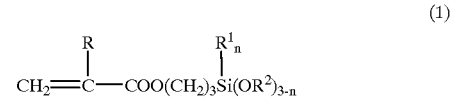

(1)

wherein R is hydrogen or methyl, $R^1$ and $R^2$ each are alkyl of 1 to 4 carbon atoms, and n is an integer of 0 to 2, said method comprising:
   distilling a reaction solution containing said acryloxy or methacryloxy-bearing alkoxysilane in a thin-layer distillation device at a temperature of 90°–160° C. and a vacuum of 1 to 15 mmHg,
   wherein said thin-layer distillation device is an upright falling-film evaporator comprising a cylindrical heating section and a wiper-like agitating blade wherein the tip of said agitating blade is centrifugally urged against the surface of said heating section for scraping the surface thereof.

21. A method for distilling an acryloxy or methacryloxy-bearing alkoxysilane represented by formula (1):

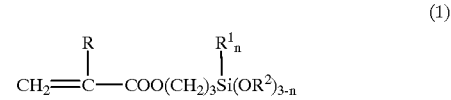

(1)

wherein R is hydrogen or methyl, $R^1$ and $R^2$ each are alkyl of 1 to 4 carbon atoms, and n is an integer of 0 to 2, said method comprising:
   distilling a reaction solution containing said acryloxy or methacryloxy-bearing alkoxysilane in a thin-layer distillation device at a temperature of 90°–160° C. and a vacuum of 1 to 15 mmHg,
   wherein concentrated residue discharged from said thin-layer distillation device is recycled back to said thin-layer distillation device.

* * * * *